United States Patent
Ueno et al.

(10) Patent No.: US 10,603,142 B2
(45) Date of Patent: Mar. 31, 2020

(54) METHOD FOR MANUFACTURING DENTAL PROSTHESIS

(71) Applicant: GC CORPORATION, Tokyo (JP)

(72) Inventors: Takayuki Ueno, Tokyo (JP); Shuntaro Urata, Tokyo (JP)

(73) Assignee: GC CORPORATION, Bunkyo-ku, Tokyo (JP)

( * ) Notice: Subject to any disclaimer, the term of this patent is extended or adjusted under 35 U.S.C. 154(b) by 212 days.

(21) Appl. No.: 15/512,871

(22) PCT Filed: Sep. 25, 2015

(86) PCT No.: PCT/JP2015/077062
§ 371 (c)(1),
(2) Date: Mar. 21, 2017

(87) PCT Pub. No.: WO2016/052321
PCT Pub. Date: Apr. 7, 2016

(65) Prior Publication Data
US 2017/0296311 A1    Oct. 19, 2017

(30) Foreign Application Priority Data
Sep. 29, 2014    (JP) .................. 2014-198111

(51) Int. Cl.
*A61C 13/00*    (2006.01)
*A61C 13/087*    (2006.01)
(Continued)

(52) U.S. Cl.
CPC ...... *A61C 13/0006* (2013.01); *A61C 13/0004* (2013.01); *A61C 13/087* (2013.01);
(Continued)

(58) Field of Classification Search
CPC .................................. A61C 13/0004
See application file for complete search history.

(56) References Cited

U.S. PATENT DOCUMENTS 3,197,866 A * 8/1965 Barron ............... A61C 13/1026
433/169
4,789,338 A * 12/1988 Eisenmann ............ A61C 13/26
433/169
(Continued)

FOREIGN PATENT DOCUMENTS

EP    0 895 774 A2    2/1999
EP    1 652 655 A2    5/2006
(Continued)

OTHER PUBLICATIONS

Translation JP2012036136A Feb. 23, 2012 (Year: 2012).*
(Continued)

*Primary Examiner* — Cachet I Proctor
(74) *Attorney, Agent, or Firm* — Sughrue Mion, PLLC

(57) ABSTRACT

An object of the present invention is to provide a method for manufacturing a dental prosthesis capable of properly arranging a dental reinforcement when a dental prosthesis made of resin where the dental reinforcement is arranged is manufactured. The method includes turning information on an intraoral shape into data: designing, in a form of data, a shape of a resin body that is a part formed of resin based on the data; designing, in the form of data, a position of a dental reinforcement that is to be arranged inside the resin body; and forming, in the form of data, a space and an opening that communicates with an outside in the position in the resin body where the dental reinforcement are to be arranged, based on the position, to design a resin body with an opening.

4 Claims, 10 Drawing Sheets

(51) Int. Cl.
*A61C 9/00* (2006.01)
*A61C 8/00* (2006.01)

(52) U.S. Cl.
CPC ............ *A61C 8/005* (2013.01); *A61C 8/0051* (2013.01); *A61C 9/0053* (2013.01)

(56) References Cited

U.S. PATENT DOCUMENTS

| | | | | |
|---|---|---|---|---|
| 5,788,498 | A * | 8/1998 | Wohlwend | A61C 13/0003 264/19 |
| 6,200,136 | B1 * | 3/2001 | Prasad | A61C 13/26 433/180 |
| 6,270,348 | B1 * | 8/2001 | Petersen | C08K 7/14 433/228.1 |
| 2002/0123023 | A1 * | 9/2002 | Sicurelli, Jr. | A61C 13/30 433/220 |
| 2006/0118990 | A1 * | 6/2006 | Dierkes | A61C 13/001 264/104 |
| 2007/0009852 | A1 | 1/2007 | Childress | |
| 2007/0196792 | A1 * | 8/2007 | Johnson | A61C 5/70 433/218 |
| 2007/0292821 | A1 * | 12/2007 | De Vreese | A61C 5/00 433/195 |
| 2008/0096166 | A1 * | 4/2008 | Morris | A61C 13/275 433/141 |

FOREIGN PATENT DOCUMENTS

| | | | | |
|---|---|---|---|---|
| EP | 1652655 A2 * | 5/2006 | ........... | A61C 13/001 |
| JP | 11-116422 A | 4/1999 | | |
| JP | 2005350421 A * | 12/2005 | ........... | A61K 6/0073 |
| JP | 2007-068821 A | 3/2007 | | |
| JP | 2012-036136 A | 2/2012 | | |
| JP | 2012036136 A * | 2/2012 | | |
| WO | 2009/068559 A1 | 6/2009 | | |
| WO | WO-2009068559 A1 * | 6/2009 | ........... | A61C 8/0048 |

OTHER PUBLICATIONS

Translation WO2009068559A1 Jun. 4, 2009 (Year: 2009).*
Takahashi et al. JP2005250421A translation retrieved from Espacenet. (Year: 2005).*
International Search Report of PCT/JP2015/077062 dated Dec. 15, 2015.

* cited by examiner

METHOD FOR MANUFACTURING DENTAL PROSTHESIS

CROSS REFERENCE TO RELATED APPLICATIONS

This application is a National Stage of International Application No. PCT/JP2015/077062 filed Sep. 25, 2015, claiming priority based on Japanese Patent Application No. 2014-198111 filed Sep. 29, 2014, the contents of all of which are incorporated herein by reference in their entirety.

TECHNICAL FIELD

This invention relates to a method for manufacturing a dental prosthesis, and more particularly relates to a method for manufacturing a dental prosthesis made of resin where a dental reinforcement is arranged.

BACKGROUND ART

For recent years, resin has been used for a dental prosthesis such as a bridge and a denture base for a false tooth according to development of dental resin material because resin has advantages of excellent aesthetics etc.

For example, a bridge is a dental prosthesis that is used when a part of teeth is lost and its root does not exist. This is a dental prosthesis that holds an artificial tooth in an space produced by a lost tooth, using a natural tooth (remaining tooth) remaining in one side of the space as a basis (abutment tooth) (or using natural teeth remaining in both sides of the space).

For example, a bridge is made as follows: prior to making a bridge, an abutment tooth is ground, to have a shape easy for a dental prosthesis to be attached to (for example, a frustoconical shape); an impression of a portion including a space produced by a lost tooth and the abutment tooth of the above described shape is taken, to obtain a counterdie of a shape of a portion for which a bridge is made; further, a plaster cast is made according to this impression, the shape is determined based on the plaster cast, to make the bridge out of resin.

When all the teeth are lost, dentures where artificial teeth are arranged on denture bases that cover alveolar ridges are provided. Resin is also used for these denture bases.

However, the mechanical strength of resin is lower than metal in tension and bending. Thus, a crack might form in some portion due to lack of the strength. For example, it is employed that lack of the strength is made up for by using a metallic frame together when a dental prosthesis is made using hard resin. However, this method takes a lot of effort.

In contrast, as shown in FIG. 1 of Patent Literature 1, such a bridge is suggested that a fiber-reinforced composite material for dental restorations which comprises glass fibers in the shape of a bar is applied to. According to this, lack of the strength of a bridge made of resin can be made up for.

Patent Literature 2 describes formation of a bridge with a fiber-reinforced composite material for dental restorations ([0009] of Patent Literature 2). According to this, a cavity to face a treatment site (a portion where a tooth is lost) is formed in each adjacent tooth that is positioned in either side of the treatment site where a tooth is lost; the glass reinforced composite material is cut longer than a distance between the cavities in both adjacent teeth, and is immersed in resin or the like to put resin-coating thereon; after that, both ends thereof are placed in the cavities in both adjacent teeth as the center part thereof is bent toward a gum; resin material is poured into both cavities, to be polymerized and cured along with the fiber-reinforced composite material for dental restorations to be fixed; after that, resin material is built up in the shape of a tooth on this fixed glass reinforced composite material and cured, to make a bridge.

CITATION LIST

Patent Literature

Patent Literature 1: JP H11-116422A
Patent Literature 2: JP 2007-68821A

SUMMARY OF INVENTION

Technical Problem

However, in the invention of Patent Literature 1, concerning employment of the fiber-reinforced composite material for dental restorations to a bridge, the fiber-reinforced composite material for dental restorations is arranged so as to be laid across occlusal surfaces of crowns (crown-shaped artificial teeth attached to abutment teeth) and an occlusal surface of a false tooth (an artificial tooth held by a lost tooth portion) with reference to FIG. 2, which is problematic in aesthetics etc.

On the other hand, in the invention of Patent Literature 2, occlusal surfaces are ground, to arrange the fiber-reinforced composite material for dental restorations, and after that, resin material is built up. Occlusal surfaces are formed by this build-up, and are not exact surfaces obtained by an impression.

It is difficult to properly arrange such a fiber-reinforced composite material for dental restorations (dental reinforcement) in a dental prosthesis in view of aesthetics, an effect of reinforcement, a shape of the dental prosthesis, and so on. For example, according to the above described Patent Literatures 1 and 2, a problem might arise in aesthetics. If a dental reinforcement is arranged in a part other than a dental prosthesis in view of aesthetics, a thin portion of a resin part is formed by a groove and/or a hole for arranging the dental reinforcement, which sometimes causes the strength to lower conversely.

An object of the present invention is to provide a method for manufacturing a dental prosthesis capable of properly arranging a dental reinforcement when a dental prosthesis made of resin where the dental reinforcement is arranged is manufactured.

Solution to Problem

The present invention will be described hereinafter.

The present invention is a method for manufacturing a dental prosthesis where a dental reinforcement is arranged inside resin, the method comprising: turning information on an intraoral shape into data; designing, in a form of data, a shape of a resin body that is a part formed of resin based on the data obtained by said turning information: designing, in the form of data, a position of a dental reinforcement that is to be arranged inside the resin body, and forming, in the form of data, a space and an opening that communicates with an outside in the position in the resin body where the dental reinforcement is to be arranged, based on the position, to design a resin body with an opening.

In this invention, strength may be calculated after said designing a position of a dental reinforcement.

This invention may further include: after said forming a space and an opening, to design a resin body with an opening, making the resin body with an opening; inserting the dental reinforcement into the resin body with an opening; and covering the opening of the resin body with an opening.

Advantageous Effects of Invention

According to the present invention, a dental reinforcement can be arranged at a proper position on a dental prosthesis made of resin in view of aesthetics, comfort and strength.

DESCRIPTION OF EMBODIMENTS

Figure 1:
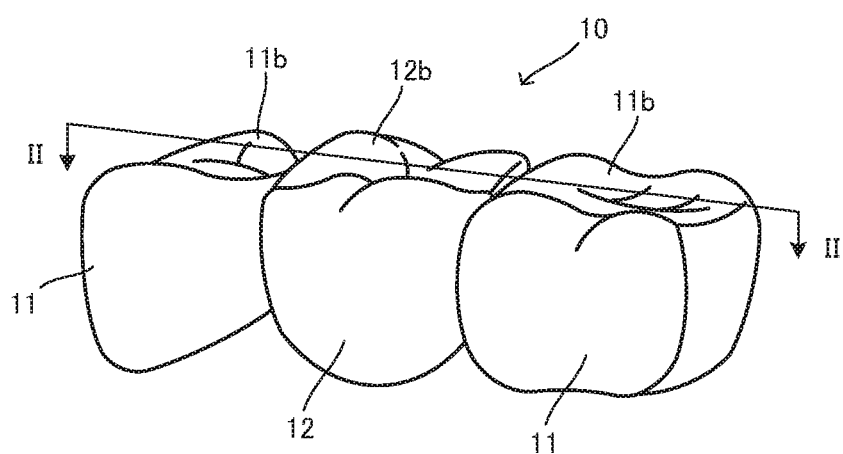
FIG. 1 is an external perspective view of a bridge 10.

The present invention will be described hereinafter based on embodiments shown in the drawings. It is noted that this invention is not limited to these embodiments.

Figure 2:
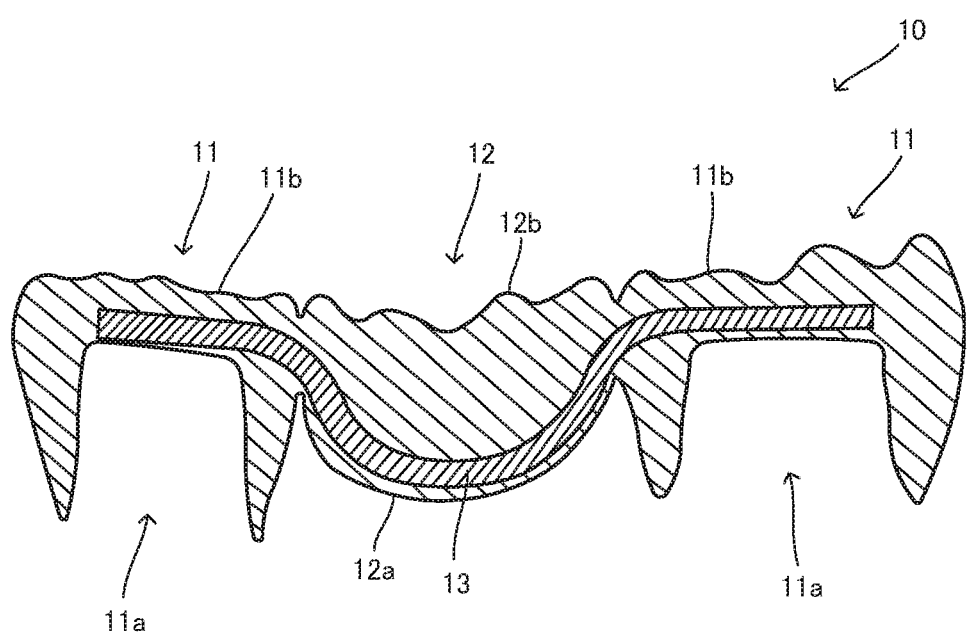
FIG. 2 is a cross-sectional view of the bridge 10.

First, a bridge 10, which is an example of a dental prosthesis manufactured according to the manufacturing method of the present invention will be described. FIG. 1 is an external perspective view of the bridge 10, and FIG. 2 is a cross-sectional view of the bridge 10 which is taken along the line II-II in FIG. 1. That is, FIG. 2 is a cross-sectional view in a direction of aligning crowns 11 and a false tooth 12.

As seen from FIGS. 1 and 2, two crowns 11 and the false tooth 12 arranged between the crowns 11 integrate, to form the bridge 10. A dental reinforcement 13 is arranged so as to be laid across the inside of these crowns 11 and the false tooth 12.

Each crown 11 is a part formed of resin, and is arranged so as to cover an abutment tooth in the bridge 10 as publicly known, whereby the false tooth 12 is held in a lost tooth portion. Therefore, a recess 11a is formed in each crown 11 in a side of the abutment tooth so as to open in the side of the abutment tooth. The abutment tooth is inserted into the recess 11a. In the opposite side of the recess 11a, an occlusal surface 11b that copies an occlusal surface of a natural tooth is formed, to reproduce functions of a natural tooth. Publicly known embodiments can be employed as the crowns 11 as described above.

The false tooth 12 is a part formed of resin, and is arranged at the lost tooth portion in an oral cavity by being held by the crowns 11. The false tooth 12 has an alveolar ridge opposite surface 12a that is arranged in a side of an alveolar ridge, and an occlusal surface 12b that is in the opposite side of the alveolar ridge opposite surface 12a. While a publicly known embodiment can also be employed as the false tooth 12, the alveolar ridge opposite surface 12a is a curved surface similar to a spherical face in this embodiment in order to prevent the alveolar ridge from being hurt. The occlusal surface 12b copies an occlusal surface of a natural tooth, to reproduce functions of a natural tooth.

As seen from FIG. 2, the dental reinforcement 13 is a board-like reinforcement member arranged inside the crowns 11 and the false tooth 12, as extending in the direction of arranging the crowns 11 and the false tooth 12. While publicly known one can be employed as the dental reinforcement 13, the dental reinforcement 13 is formed of material that can reinforce resin, such as glass fibers and a metallic plate.

The arrangement of the dental reinforcement 13 is determined in the method for manufacturing a dental prosthesis described below. In this embodiment, the dental reinforcement 13 is arranged closer to the recesses 11a of the crowns 11 and the alveolar ridge opposite surface 12 of the false tooth 12, which are in the opposite side of the occlusal surfaces 11b and 12b. Whereby, the occlusal surfaces 11b of the crowns 11 can be reproduced without changing occlusal surfaces obtained by impression taking, which makes it possible to obtain proper occlusion.

The bridge 10 deforms in such a way that the false tooth 12 is pushed toward the alveolar ridge side upon occlusion. Thus, it is preferable that the dental reinforcement 13 be arranged in the side of the alveolar ridge opposite surface 12a also in view of reinforcement.

Next, the method for manufacturing a dental prosthesis S1 (hereinafter may be referred to as "manufacturing method S1") according to one embodiment will be described. Here, to manufacture the bridge 10 will be described as an example for easy understanding. However, the manufacturing method S1 can be employed for manufacturing other types of dental prostheses.

Figure 3:
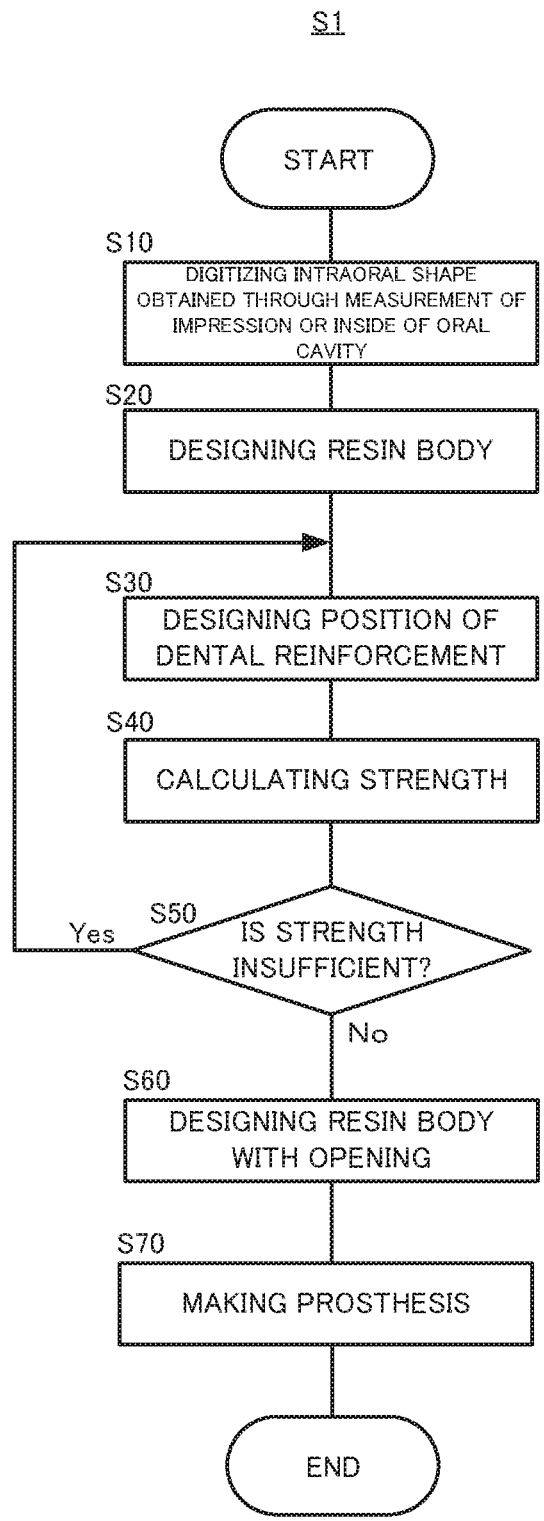
FIG. 3 is a flowchart of a method for manufacturing a dental prosthesis S1.

FIG. 3 is a flowchart showing the flow of the manufacturing method S1. As seen from FIG. 3, the manufacturing method S1 includes a step of digitizing an intraoral shape S10, a step of designing a resin body S20, a step of designing a position of a dental reinforcement S30, a step of calculating strength S40, a step of determining strength S50, a step of designing a resin body with an opening S60, and a step of making a prosthesis S70. Hereinafter each step will be described. Prior to the step of digitizing an intraoral shape S10, abutment teeth shall be ground by a publicly known method, and if needed (if digitized data is obtained from an impression), an impression based on this state shall be taken.

Figure 4:
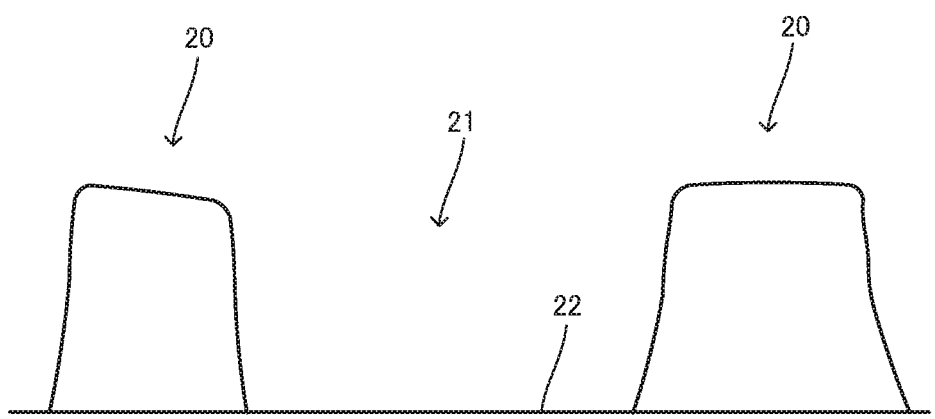
FIG. 4 shows a step of digitizing an intraoral shape S10.

In the step of digitizing an intraoral shape S10, information on an intraoral shape is turned into data. Examples of a means of turning the information into data include measuring the taken impression, measuring a model made from the impression, and directly measuring the inside of an oral cavity. Data of the shape obtained through such measurement is turned into CAD data. A method of obtaining CAD data can be carried out with a publicly known device. For example, a three-dimensional optical scanner can be used. Whereby, for example as shown in FIG. 4, such information is turned into data as forms of and positional relationship between two abutment teeth 20, a lost tooth portion 21 that is a space formed between the abutment teeth 20, and an alveolar ridge 22, which enables the information to be calculated.

Figure 5:
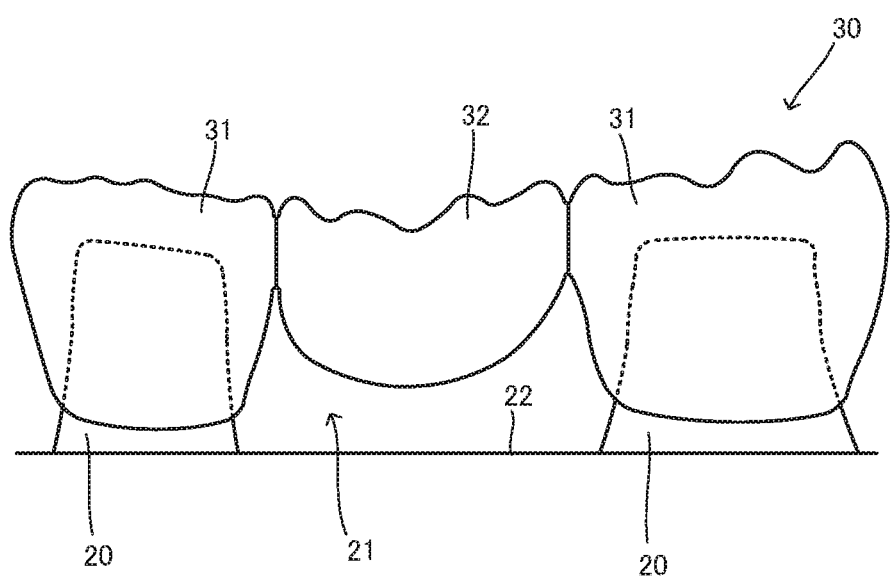
FIG. 5 shows a step of designing a resin body S20.

In the step of designing a resin body S20, a shape of a resin body 30 is determined in the form of data as shown in FIG. 5 based on the data obtained in the step of digitizing an intraoral shape S10. The resin body 30 has a form including crowns 31 and false tooth 32 except a dental reinforcement. At this time, a position of a dental reinforcement is not determined yet. While non-limiting methods of determining a shape of the resin body 30 in this step are used, such a method can be employed that selection is made based on shapes obtained through a database where a plurality of typical forms are stored, and the selected shape is combined with the shape of an occlusal surface that had been obtained in advance before the abutment teeth 20 were ground.

Figure 6:
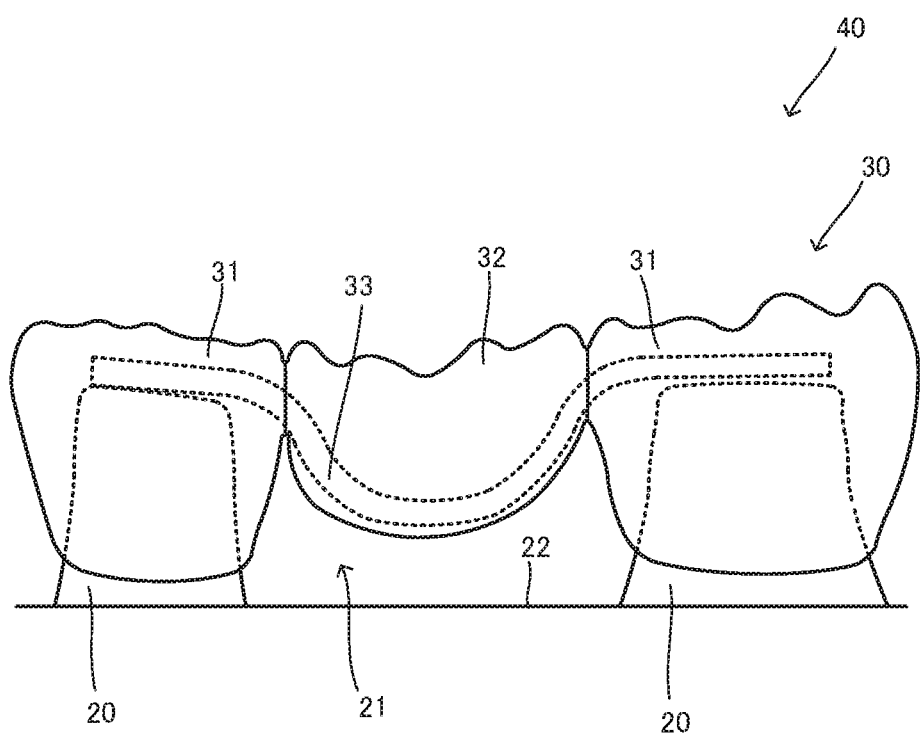
FIG. 6 shows a step of designing a position of a dental reinforcement S30.

The step of designing a position of a dental reinforcement S30 is a step of determining a position of a dental reinforcement in the resin body 30 obtained in the step of designing a resin body S20, in the form of data. Whereby, as shown in FIG. 6, a bridge 40 that is the resin body 30 where a dental reinforcement 33 is arranged is obtained in the form of data.

A position of the dental reinforcement is determined to be arranged so as to reinforce a portion where a crack or the like forms upon applying occlusal pressure. At this time, it is important to take the thickness of the resin body 30 around the dental reinforcement 33 and the material of resin into consideration.

The step of calculating strength S40 is a step of calculating strength of the bridge 40 obtained in the step of designing a position of a dental reinforcement S30. Whereby, the strength can be confirmed, and the effect of the reinforcement can be further surely confirmed. Publicly known simulation software can be used for the strength calculation.

When the step of calculating strength S40 is carried out, the strength is evaluated in the step of determining strength S50. If the strength is insufficient, the process returns to the step of designing a position of a dental reinforcement S30, and the form and the position of the dental reinforcement are changed. If there is no problem in the strength, the process goes on to the following step.

It is noted that the step of calculating strength S40 is not necessarily carried out on a dental prosthesis all the time. If the step S40 is not carried out, the process can go on to the step of designing a resin body with an opening S60, skipping the step of calculating strength S40 and the step of determining strength S50.

Figure 7:
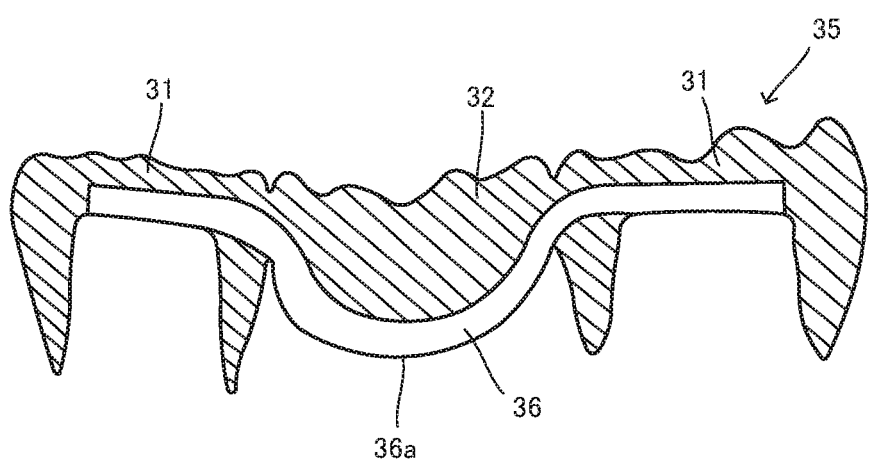
FIG. 7 shows a step of designing a resin body with an opening S60.

The step of designing a resin body with an opening S60 is a step of designing a resin body with an opening 35 that has a space and an opening for embedding the dental reinforcement 13 when the bridge 10 is manufactured. FIG. 7 shows this. As shown in FIG. 7, a dental reinforcement arrangement space 36 that has an opening 36a is formed in the resin body 30 obtained in the step of designing a resin body S20, in the form of data in order that the dental reinforcement can be inserted into the position determined in the step of designing a position of a dental reinforcement S30, to be the resin body with an opening 35. Whereby, the dental reinforcement can be properly arranged.

Some methods are considered as means for filling this opening 36a in the end. Examples include: a method of filling the space 36 with resin before curing, and then curing the resin; a method of closing a lid made of resin to cover the opening 36a (at this time, a member to be the lid is separately made in the form of data as well); and a method of forming a plurality of parts into the resin body 30, one of which is the resin body with an opening 35, and combining the one with the other parts, to cover the opening 36a.

Figure 8:
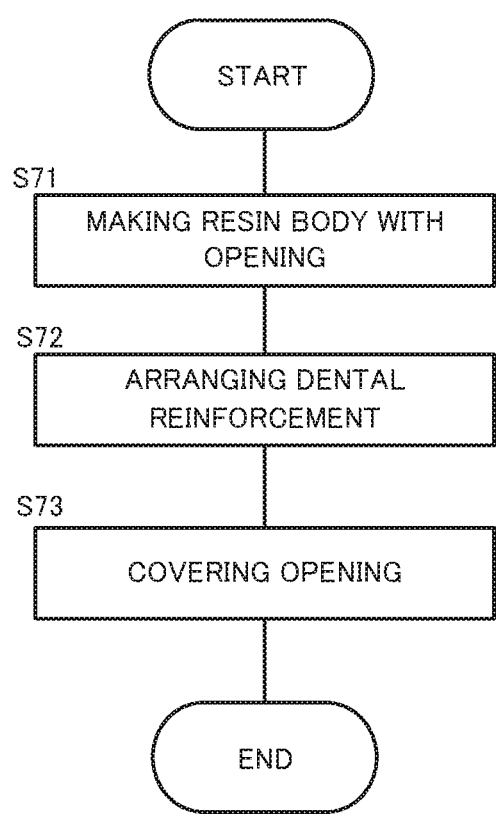
FIG. 8 is a flowchart of a step of making a prosthesis S70.

The step of making a prosthesis S70 is a step of making the resin body with an opening 35 obtained in the form of data in the step of designing a resin body with an opening S60, with a tool device. FIG. 8 shows a flowchart of procedure of the step of making a prosthesis S70. As seen from FIG. 8, the step of making a prosthesis S70 includes a step of making a resin body with an opening S71, a step of arranging a dental reinforcement S72 and a step of covering an opening S73.

In the step of making a resin body with an opening S71, an actual resin body with an opening 15 is made based on the resin body with an opening 35 obtained in the form of data in the step of designing a resin body with an opening S60. Thus, in the resin body with an opening 15, a dental reinforcement arrangement space 16 corresponding to the dental reinforcement arrangement space 36, and an opening 16a corresponding to the opening 36a are formed (see FIG. 9). The resin body with an opening 15 can be made by cutting-out or the like with an NC machine tool.

Figure 9:
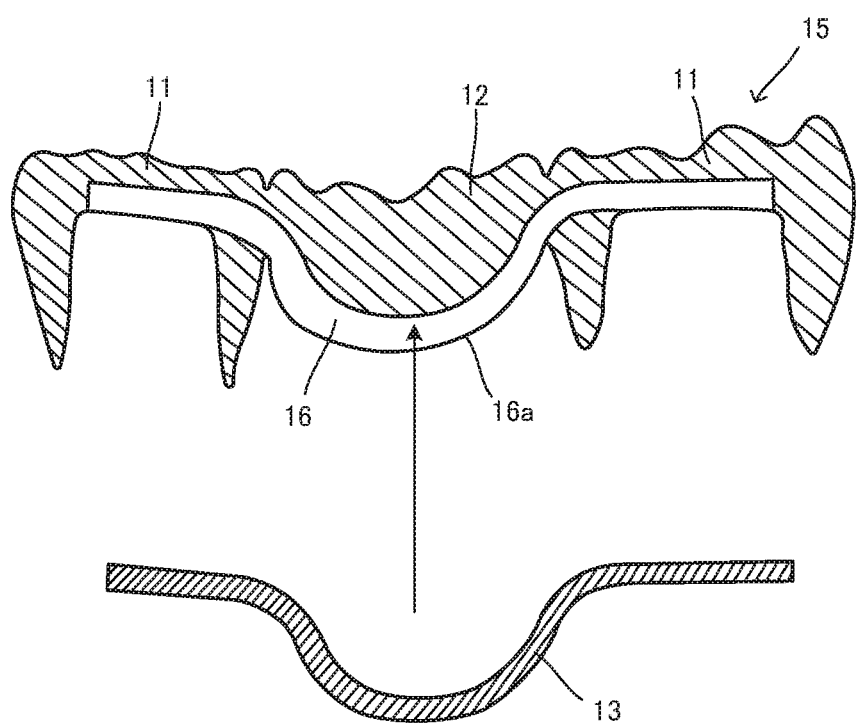
FIG. 9 shows a step of arranging a dental reinforcement S72.

The step of arranging a dental reinforcement S72 is, as shown in FIG. 9, a step of arranging the dental reinforcement 13 in the resin body with an opening 15 obtained in the step of making a resin body with an opening S71. In this invention, the dental reinforcement 13 can be easily arranged because the dental reinforcement arrangement space 16 and the opening 16a for arranging the dental reinforcement 13 are provided with the resin body with an opening 15 in advance.

The step of covering the opening S73 is a step of covering the opening with a proper method. Examples include: a method of filling the dental reinforcement arrangement space 16 with resin before curing, and then curing the resin; a method of closing a lid made of resin to cover the opening 16a (at this time, a member to be the lid is separately made as well); and a method of forming a plurality of parts, one of which is the resin body with an opening 15, and combining the one with the other parts, to cover the opening 16a.

According to the above described manufacturing method S1, the bridge 10 can be obtained. According to the manufacturing method S1, the dental reinforcement 13 can be arranged anywhere except a portion where causes a problem about aesthetics or a portion necessary to be avoided. At this time, for example, processing can be done on the data using CAD/CAM. Thus, it is possible to efficiently prevent the strength from erroneously lowering even if the shape is complicated. Further, the improvement of the strength can be more efficiently achieved by including the step of calculating strength S40.

Figure 10:
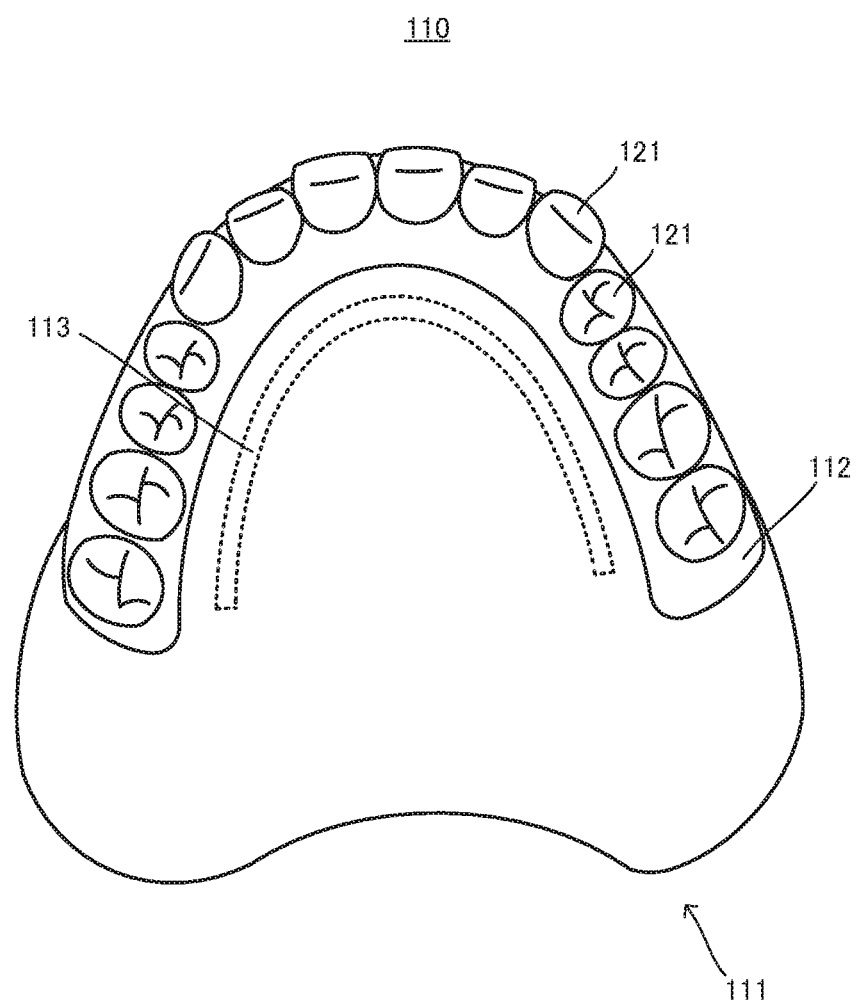
FIG. 10 is an external view of a denture 110.

FIG. 10 shows a dental prosthesis according to another example made with the manufacturing method S1. A dental prosthesis of this example is a denture 110. A dental reinforcement 113 is arranged inside a denture base 111.

The denture 110 is composed of the denture base 111, the dental reinforcement 113 and a plurality of artificial teeth 121.

The denture base 111 is a member that has functions of holding the artificial teeth 121 in predetermined positions, and stably attaching the denture itself onto an oral mucosa. As seen from FIG. 10, the denture base 111 includes a ridge part 112 that rises like a ridge as a portion where the artificial teeth 121 are arranged, and the artificial teeth 121 are arranged along this ridge part 112.

The dental reinforcement 113 is the same as the dental reinforcement 13 described above. In this example, the dental reinforcement 113 is arranged inside the denture base 111, closer to the side where the artificial teeth 121 are arranged. Whereby, it can be prevented that the dental reinforcement 113 hurts a surface of a use's mucosa. In view of the improvement of strength, the dental reinforcement 113 has a shape like an arc along the direction where the artificial teeth 121 are arranged.

The artificial teeth 121 are artificial teeth made so as to have the function of natural teeth that is lost, instead of the natural teeth. The artificial teeth 121 are arranged along the ridge part 112 of the denture base 111 like an arc, that is, like a row of teeth, and function as natural teeth.

REFERENCE SIGNS LIST

10 bridge (dental prosthesis)
11 crown
12 false tooth (artificial tooth)
11*a* recess
11*b* occlusal surface
12*a* alveolar ridge opposite surface 12*a*
12*b* occlusal surface
13 dental reinforcement
20 abutment tooth
21 lost tooth portion
22 alveolar ridge
30 resin body
31 crown
32 false tooth
33 dental reinforcement
35 resin body with an opening
36 space
36*a* opening

The invention claimed is:

1. A method for manufacturing a dental prosthesis where a dental reinforcement is arranged inside a resin and a plurality of false teeth, the method comprising:
   turning information on an intraoral shape into data;
   designing, in a form of data, a shape of a resin body that is a part formed of resin based on the data;
   designing, in the form of data, a position of a dental reinforcement that is formed of fibers and is to be arranged inside the resin body and is extending in the direction of arranging the false teeth;
   forming, in the form of data, a space and an opening that communicates with an outside in the position in the resin body where the dental reinforcement is to be arranged extending in the direction of arranging the false teeth, on the opposite surface of the false teeth from an occlusal surface, based on the position, to design a resin body with an opening;
   making the resin body with an opening, based on the designing of the resin body with an opening, and arranging the dental reinforcement formed of fibers in the opening of the resin body with an opening; and
   covering the opening with resin after arranging the dental reinforcement.

2. The method according to claim 1, further comprising: calculating strength after said designing a position of a dental reinforcement.

3. The method according to claim 1, further comprising:
   after said forming a space and an opening, to design a resin body with an opening,
   making the resin body with an opening;
   inserting the dental reinforcement into the resin body with an opening; and
   covering the opening of the resin body with an opening.

4. The method according to claim 1, wherein the dental reinforcement is formed in a board shape.

\* \* \* \* \*